United States Patent
Stragies et al.

(10) Patent No.: US 11,672,750 B2
(45) Date of Patent: Jun. 13, 2023

(54) DERMAL FILLER BASED ON CROSSLINKED HYALURONIC ACID, CALCIUM PHOSPHATE MATERIAL PARTICLES AND CARBOXYMETHYL CELLULOSE, A PROCESS FOR PREPARING SAME AND USES THEREOF

(71) Applicant: Merz Pharma GmbH & Co. KGaA, Frankfurt am Main (DE)

(72) Inventors: Roland Stragies, Berlin (DE); Nadine Hagedorn, Frankfurt am Main (DE); Lubin Belkovi, Friedrichsdorf (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 0 days.

(21) Appl. No.: 17/046,094

(22) PCT Filed: Apr. 12, 2019

(86) PCT No.: PCT/EP2019/059415
§ 371 (c)(1),
(2) Date: Oct. 8, 2020

(87) PCT Pub. No.: WO2019/197608
PCT Pub. Date: Oct. 17, 2019

(65) Prior Publication Data
US 2021/0030657 A1    Feb. 4, 2021

(30) Foreign Application Priority Data
Apr. 13, 2018   (EP) .................................... 18167286

(51) Int. Cl.
| | | |
|---|---|---|
| *A61Q 19/08* | (2006.01) | |
| *A61Q 19/00* | (2006.01) | |
| *A61K 31/728* | (2006.01) | |
| *A61K 31/167* | (2006.01) | |
| *A61K 8/24* | (2006.01) | |
| *A61K 47/38* | (2006.01) | |
| *A61K 31/765* | (2006.01) | |
| *A61K 8/73* | (2006.01) | |
| *A61K 8/04* | (2006.01) | |
| *A61K 8/42* | (2006.01) | |

(52) U.S. Cl.
CPC .............. *A61K 8/735* (2013.01); *A61K 8/042* (2013.01); *A61K 8/24* (2013.01); *A61K 8/42* (2013.01); *A61K 8/731* (2013.01); *A61Q 19/08* (2013.01); *A61K 2800/412* (2013.01); *A61K 2800/54* (2013.01); *A61K 2800/87* (2013.01); *A61K 2800/91* (2013.01)

(58) Field of Classification Search
CPC .. A61L 2400/06; A61L 2430/34; A61L 27/50; A61L 27/26; A61L 27/362; A61Q 19/08; A61Q 19/00; A61Q 19/001; A61K 2800/91; A61K 81/735; A61K 8/042; A61K 9/0021; A61K 9/0019; A61K 31/728; A61K 8/24; A61K 8/735; A61K 8/731; A61K 31/738; A61K 31/167; A61K 47/38; A61K 33/42
See application file for complete search history.

(56) References Cited

U.S. PATENT DOCUMENTS

2017/0333596 A1   11/2017   Hagedorn et al.

FOREIGN PATENT DOCUMENTS

| EP | 1080698 A1 | 3/2001 | |
|---|---|---|---|
| WO | 2014056722 A2 | 4/2014 | |
| WO | 2014056723 A1 | 4/2014 | |
| WO | 2016074794 A1 | 5/2016 | |
| WO | WO-2017136935 A1 * | 8/2017 | ............... C08L 5/08 |

OTHER PUBLICATIONS

Natalia G. Lapatina and Tatiana Pavlenko, "Diluted calcium hydroxylapatite for skin tightening of the upper arms and abdomen," Journal of drugs in dermatology: JDD, (2017), vol. 16, No. 9 : 900-906.
International Search Report for Application No. PCT/EP2019/059415 dated Jun. 19, 2019.

* cited by examiner

*Primary Examiner* — Tracy Liu
(74) *Attorney, Agent, or Firm* — McBee Moore & Vanik IP, LLC

(57) ABSTRACT

The present invention relates to a dermal filler composition based on crosslinked hyaluronic acid, calcium phosphate material particles and carboxymethyl cellulose. The present invention further provides a process for preparing said dermal filler composition, and its use in cosmetic treatments such as for improvement of skin quality.

15 Claims, No Drawings

DERMAL FILLER BASED ON CROSSLINKED HYALURONIC ACID, CALCIUM PHOSPHATE MATERIAL PARTICLES AND CARBOXYMETHYL CELLULOSE, A PROCESS FOR PREPARING SAME AND USES THEREOF

CROSS-REFERENCE TO RELATED APPLICATIONS

This application is the National Stage entry of International Application No. PCT/EP2019/059415, filed 12 Apr. 2019, which claims priority to European Patent Application No. 18167286.6, filed 13 Apr. 2018.

BACKGROUND

Field of the Invention

The present invention relates to a dermal filler composition based on crosslinked hyaluronic acid, calcium phosphate material particles and carboxymethyl cellulose. The present invention further provides a process for preparing said dermal filler composition, and its use in cosmetic treatments such as for improvement of skin quality.

Description of Related Art

Dermal fillers have become increasingly popular in the past years because they offer anti-ageing and skin remodeling treatments previously only achievable with surgery. Dermal fillers are used in the form of a hydrogel that can be injected into the skin. They are therefore substantially cheaper, safer and more painless than surgical cosmetic procedures.

There are various types of dermal fillers available on the market today. The most common types are fillers based on calcium hydroxyapatite (e.g., Radiesse®), hyaluronic acid (e.g., Restylane®, Perlane®, Juvéderm®, Prevelle™, Esthélis™, Belotero®), polyalkylimide (Aquamid®), polylactic acid (PLLA; Sculptra®), and polymethyl-methacrylate microspheres (PMMA; Bellafill®). Upon injection, these fillers act as filling materials to provide volume to the skin, thereby providing the desired aesthetic effect of improving the skin's contour (e.g., enhance fullness of cheeks, plump thin lips, enhance cheekbone etc.) and reducing depressions in the skin due to scars, injury or lines (e.g., wrinkles and folds caused by ageing such as crow's feet, marionette lines, and nasolabial folds).

The commercial product marketed as Radiesse® (hereinafter Radiesse) is a dermal filler comprising calcium hydroxyapatite (CaHA) particles, carboxymethyl cellulose (CMC) gel and glycerin. This particulate dermal filler is used for subdermal implantation for the correction of moderate to severe facial wrinkles and folds, such as nasolabial folds. When it is injected, the gel that carries the CaHA particles fills areas that have lost volume, providing a lifting effect shortly after treatment. The gel is dissipated in vivo over time and replaced with soft tissue growth, while the calcium hydroxyapatite remains at the site of injection and stimulates the production of collagen in the skin. In other words, Radiesse provides an immediate volumizing effect as well as long-term collagen stimulation, resulting in an improvement of the skin's elasticity and firmness.

In clinical practice, Radiesse is often diluted with lidocaine or saline to add anesthetic properties to the dermal filler and/or change its flow and viscoleastic properties. Physicians have developed their own best practice for how much lidocaine or saline is added depending on the body site being treated which often includes off-label uses. Diluted Radiesse has been shown in several studies to allow for long-term skin rejuvenation by neocollagenesis. It was also observed that elastin expression increased in parallel with collagen and that there was also increased angiogenesis, suggesting a dermal remodeling that was accompanied by outgrowth of new blood vessels.

Furthermore, more recent research has discovered that the collagen-stimulating properties of dilutions of Radiesse either with lidocaine or saline can be used for skin-tightening procedures. The effectiveness and safety of diluted Radiesse for skin tightening in cases of skin laxity was confirmed in a recent study (Lapatina, N. G. and Pavlenko, T. J., Drugs Dermatol. 2017; 16(9):900-906). It was found that diluted Radiesse improves skin elasticity and increases dermal thickness in the upper arms and abdomen. The procedures were well tolerated and subject and investigator satisfaction with treatment results was very high. Thus, the ability of diluted Radiesse to induce remodeling of the extracellular matrix after subdermal injection offers significant potential for skin tightening procedures in clinical practice.

The core technologies used in Radiesse are covered by multiple patents such as European patent No. 1 080 698, filed in 1993, which discloses injectable soft tissue augmentation materials comprising a matrix of rounded, substantially spherical, biocompatible, substantially non-resorbable, finely divided ceramic particles (e.g., CaHA). Furthermore, the use of CMC as a lubricant in dermal fillers based on crosslinked hyaluronic acid is disclosed in WO 2016/074794. This document also discloses the optional presence of resorbable biocompatible microparticles in the dermal filler composition. In addition, WO 2014/056722 describes an injectable, sterile aqueous formulation for aesthetic use in the form of a particulate cohesive viscoelastic gel, comprising crosslinked hyaluronic acid (HA) and hydroxyapatite particles having an average size of 200 µm or less at a concentration of between 5% and 60% (w/v). Similarly, WO 2014/056723 describes an injectable, sterile aqueous formulation for therapeutic use in the form of a particulate cohesive viscoelastic gel, comprising crosslinked hyaluronic acid (HA) and hydroxyapatite particles having an average size of 650 µm or less at a concentration of between 10% and 70% (w/v).

Even though there are known dermal filler products based on calcium hydroxyapatite (CaHA) particles and carboxymethyl cellulose (CMC), or on CaHA particles and crosslinked HA, none of them shows the unique "liquid like" properties of diluted Radiesse. Dilutions of Radiesse, however, then again suffer from the drawback that they are not stable over time due to separation of the CaHA particles. This separation generally occurs after hours or even after several minutes, depending on the dilution ratio of the diluted Radiesse formulation, resulting in a significant deterioration of filler product performance.

OBJECT OF THE INVENTION

In view of the above, it is the object of the present invention to provide a dermal filler composition in which particles of a calcium phosphate material are stably suspended, while at the same time exhibiting comparable desirable properties as Radiesse.

SUMMARY OF THE INVENTION

The above object is solved by the provision of a dermal filler composition comprising a combination of crosslinked hyaluronic acid (HA) and carboxymethyl cellulose (CMC), which combination is capable of forming a gel carrier suitable for suspending CaHA particles in a stable manner, i.e. without settling or separation. This new type of dermal filler combines the advantages of Radiesse (neocollagenesis due to calcium hydroxyapatite particles) while exhibiting the unique "liquid like" properties of diluted Radiesse without undergoing separation of the CaHA particles over time.

In a first aspect of the present invention, there is provided a dermal filler composition comprising 0.50-0.95% (w/v) crosslinked hyaluronic acid, 20-55% (w/v) calcium phosphate material particles, preferably calcium hydroxyapatite particles, and 0.25-0.65% (w/v) carboxymethyl cellulose, wherein the crosslinked hyaluronic acid is crosslinked with 1,4-butanediol diglycidyl ether (BODE), and wherein at least 90% (w/w) of the calcium phosphate material particles have a particle size of less than 60 μm, preferably 45 μm or less or less than 25 μm, or from 25 μm to 45 μm.

In a second aspect of the present invention, there is provided a process for preparing a dermal filler composition of the present invention, the process comprising:
(a) preparing a crosslinked hyaluronic acid gel using 1,4-butanediol diglycidyl ether (BODE) as crosslinking agent,
(b) mixing the crosslinked hyaluronic acid gel prepared in step (a) with carboxymethyl cellulose, or a salt thereof, and calcium phosphate material particles of which at least 90% (w/w) have a particle size of less than 60 μm, preferably 45 μm or less or less than 25 μm, or from 25 μm to 45 μm, and optionally
(c) sterilizing the dermal filler composition by moist heat.

In a third aspect of the present invention, there is provided a prefilled syringe (e.g., a ready-to-use syringe), or a part thereof (e.g., a syringe barrel), filled with a dermal filler composition of the present invention.

In fourth aspect of the present invention, there is provided a kit comprising a prefilled syringe, or a part thereof, according to the present invention, and optionally instructions for use.

In a fifth aspect, the present invention relates to the use of a dermal filler composition of the present invention for cosmetic treatments, in particular for improvement of skin quality or reduction of wrinkles or lines, in particular smoothing out facial lines or wrinkles.

In a sixth and last aspect of the present invention, there is provided a method for filling or increasing the volume of a biological tissue, e.g. skin, comprising administering to a subject in need thereof an effective amount of the dermal filler composition of the present invention.

Specific embodiments of the present invention are set forth in the appended claims. The objects, advantages and features of the present invention will become more apparent in view of the following detailed description of the invention and the examples.

DETAILED DESCRIPTION OF THE INVENTION

The present invention is based on the unexpected finding that crosslinked hyaluronic acid (HA) in combination with carboxymethyl cellulose (CMC) enables the provision of a dermal filler composition in which calcium hydroxyapatite (CaHA) particles are stably suspended over time without undergoing phase separation, despite the composition's desirable low viscosity and extrusion force. The crosslinked HA provides a stronger rheological profile as compared to conventionally used non-crosslinked CMC at similar concentration and has a long in vivo persistence of up to 24 months. Overall, the dermal filler composition of the present invention provides an optimal balance of volumizing capacity, longevity and ease of injection.

In fact, the dermal filler composition of the present invention combines the advantages of Radiesse (i.e. necollagenesis due to CaHA particles) and the unique "liquid" like characteristics of diluted Radiesse (e.g., Radiesse diluted 1:1 with water-for-injection (WFI)), while effectively keeping the CaHA particles in suspension. This enables the presentation of a dermal filler composition having similar properties like diluted Radiesse in the form of a stable and safe ready-to-use prefilled syringe format, thereby avoiding problems like product loss or contamination encountered when diluting Radiesse. Moreover, the crosslinked HA in the composition of the present invention advantageously allows for filler correction by enzymatic degradation using known hyaluronidases, if required or desired In a first aspect, the present invention relates to a dermal filler composition comprising 0.50-0.95% (w/v) crosslinked hyaluronic acid, 20-55% (w/v) calcium phosphate material particles and 0.25-0.65% (w/v) carboxymethyl cellulose. In accordance with the present invention, the crosslinked hyaluronic acid is crosslinked with 1,4-butanediol diglycidyl ether (BDDE) and at least 90% (w/w) of the calcium phosphate material particles have a particle size of less than 60 urn.

The term "dermal filler" or "dermal filler composition" broadly refers to a material or composition designed to add volume to areas of soft tissue deficiency, in particular skin soft tissue deficiency. The term "soft tissue" generally relates to tissues that connect, support, or surround other structures and organs of the body. As used herein, the term "dermal filler" or "dermal filler composition" should not be construed as imposing any limitations as to the location and type of injection. The dermal filler composition of the present invention is generally "injectable", which means that it can be injected from syringes under normal conditions under normal pressure into or below the skin in order to bring the dermal filler composition to the desired target site.

Generally, a dermal filler composition as described herein is in the form of a gel, more specifically a hydrogel. It typically comprises a physiologically acceptable carrier fluid, in particular a buffered physiological saline. Further, since the injectable dermal filler composition of the present invention is intended for insertion into the human body, the pH is generally in the range of 6.5 to 7.5, preferably in the range of 6.8 to 7.4.

As used herein, the term "hyaluronic acid" or "HA" is intended to mean hyaluronic acid, hyaluronate, and any hyaluronate salt thereof, such as sodium hyaluronate, unless otherwise stated. Likewise, the term "carboxymethyl cellulose" or "CMC" is intended to mean carboxymethyl cellulose and any salt thereof, such as sodium carboxymethyl cellulose (NaCMC), unless otherwise stated.

The term "calcium phosphate material particles", as used herein, broadly refers to any particles (made) of a calcium phosphate material as defined herein below. The term "particle size", as used herein, refers to the average diameter of the calcium phosphate material particles. The average diameter can be, for example, estimated from SEM images.

In accordance with the present invention, the crosslinked hyaluronic acid is preferably contained in the dermal filler composition in an amount of 0.50-0.90% (w/v), 0.55-0.85%

(w/v), 0.60-0.85% (w/v) or 0.60-0.80% (w/v), more preferably in an amount of 0.65-0.80% (w/v), 0.70-0.80% (w/v) or 0.70-0.75% (w/v).

The hyaluronic acid used for preparation of the crosslinked HA, may have an average molecular weight of between $0.5 \times 10^6$ Da and $4.5 \times 10^6$ Da. A particularly suitable molecular weight is between $1.0 \times 10^6$ Da and $4.0 \times 10^6$ Da, between $1.5 \times 10^6$ Da and $3.5 \times 10^6$ Da or between $2.0 \times 10^6$ Da and $3.0 \times 10^6$ Da.

Within the present invention, the hyaluronic acid may be a mixture of two or more hyaluronic acids having different average molecular weights. For example, the crosslinked hyaluronic acid may be prepared by crosslinking a first hyaluronic acid having an average molecular weight of $0.1 \times 10^6$ Da to less than $1.0 \times 10^6$ Da and a second hyaluronic acid having an average molecular weight of more than $1.0 \times 10^6$ Da to $4.5 \times 10^6$ Da. Alternatively, the first and the second hyaluronic acid may be both high molecular weight HAs having an average molecular weight of more than $1.0 \times 10^6$ Da, wherein the difference in the average molecular weight is at least $0.5 \times 10^6$ Da, preferably $1.0 \times 10^6$ Da or more.

The average molecular weight of HA can be determined by intrinsic viscosity measurements, capillary electrophoresis (CE), high performance gel permeation chromatography (HPGPC), and multi-angle laser light scattering combined with size-exclusion chromatography (SEC-MALLS). Within the framework of the present invention, the average molecular weight is preferably the viscosity average molecular weight ($M_\eta$) which can be calculated from the intrinsic viscosity using the Mark-Houwink equation:

$$[\eta] = K \times M_\eta^a,$$

with $[\eta]$=intrinsic viscosity in m³/kg, $M_\eta$=viscosity average molecular weight, $K=2.26 \times 10^{-5}$, and $a=0.796$, wherein the intrinsic viscosity may be measured according to the procedure defined in European Pharmacopoeia 7.0 (Hyaluronic Acid monograph No. 1472, 01/2011).

Within the framework of the present invention, the hyaluronic acid is crosslinked with BDDE (1,4-butanediol diglycidyl ether). The degree of modification (DoM), expressed as the ratio of the sum of mono- and double-linked BDDE-crosslinkers to the sum of hyaluronic acid disaccharide units, is not particularly limited but is generally in the range of from 0.5% to 25%, preferably from 1.0% to 15%, 2.0% to 10%, or 3.0% to 8.0%.

The degree of modification can be determined by NMR in accordance with methods known in the art (Edsman et al., Gel Properties of Hyaluronic Acid Dermal Fillers, Dermatol. Surg. 2012, 38:1170-1179; Guarise et al., SEC determination of cross-link efficiency in hyaluronan fillers, Carbohydrate Polymers 2012, 88:428-434; Kenne et al., Modification and cross-linking parameters in hyaluronic acid hydrogels—Definitions and analytical methods, Carbohydrate Polymers 2013, 91:410-418).

In brief, the dialyzed and sterilized gels are degraded before conducting the NMR measurement. The degradation can be performed by chondroitinase AC (Edsman et al., supra; Kenne et al., supra), NaOH (Guarise et al., supra), addition of hyaluronidase (e.g., 150 U ovine hyaluronidase to 1 g of gel) or by incubation at 90° C. for at least 35 h. The obtained solutions are then lyophilized, dissolved in $D_2O$, and well homogenized.

The NMR measurement can be performed at, e.g., 500 MHz, at a pulse of 20 degree with several repetitions at ambient temperature to receive a spectrum with appropriate resolution. In accordance with the literature, the degree of modification (MoD) is assessed by calculating the ratio of the N-acetyl signals of HA to the methylene signals of BDDE. For N-acetyl of HA, the critical signals are located at about 2.0 ppm and at about 1.6 ppm for BDDE when solubilized in $D_2O$. In order to calculate the degree of modification, the integral values were identified and the ratio of protons of 3H of N-acetyl ($CH_3$) to 4H of methylene ($CH_2CH_2$) needs to be taken in account, in accordance with the literature (Edsman et al., supra, and Kenne et al., supra).

The crosslinked hyaluronic acid used within the present invention is not restricted to a particular crosslinking process and includes, for example, single-crosslinked, double-crosslinked or triple-crosslinked HA, and polydensified HA, i.e. crosslinked HA having a varying degree of crosslinking, typically having denser parts (higher degree of crosslinking) and less dens parts (lower degree of crosslinking).

In accordance with the present invention, the calcium phosphate material particles are contained in the dermal filler composition in an amount of 20-55% (w/v) or 25-45% (w/v), preferably in an amount of 30-45% (w/v) or 30-40% (w/v), more preferably in an amount of 30-35% (w/v) or 35-40% (w/v).

At least 90% (w/w) of the calcium phosphate material particles, i.e. 90% by weight of the particles based on the total weight of the calcium phosphate material particles, have a particle size of less than 60 μm, in particular 10-60 μm or 15-50 μm, preferably 45 μm or less, more preferably less than 25 μm or between 25 μm and 45 μm. The shape of the calcium phosphate material particles used within the present invention is not particularly limited. Typically, the calcium phosphate material particles are substantially rounded or spherical particles.

Suitable calcium phosphate material particles include, but are not limited to, calcium hydroxyapatite, calcium fluoroapatite, calcium chloroapatite, calcium carbonate apatite, tetracalcium phosphate, calcium pyrophosphate, tricalcium phosphate and octacalcium phosphate particles, and mixtures thereof. Particularly suitable for use herein are calcium hydroxyapatite particles, especially those with a particles size as mentioned above, especially of from 25 μm to 45 μm or, alternatively, of less than 25 μm.

In accordance with the present invention, the concentration of the carboxymethyl cellulose (CMC) in the dermal filler composition is 0.25-0.65% (w/v), preferably 0.30-0.60% (w/v) or 0.35-0.55% (w/v), more preferably 0.40-0.50% (w/v). The CMC forms a gel matrix for the calcium phosphate material particles.

The average molecular weight of the CMC is not particularly limited but is preferably in the range of $5.0 \times 10^4$ Da (low viscosity CMC) to $1.5 \times 10^6$ Da (high viscosity CMC), for example a molecular weight in the range of $9.0 \times 10^4$ Da to $7.0 \times 10^5$ Da, in particular in the range of $1.5 \times 10^5$ to $5.0 \times 10^5$ Da.

Suitable CMCs for use herein may be selected from a low viscosity CMC having a viscosity of 75 mPa·s to 750 mPa·s, as measured with a Brookfield spindle viscometer (model LVT) at 25° C. and a rotary speed of 60 rpm with spindles of size No. 1 or No. 2 using a 2% aqueous solution, a medium viscosity CMC having a viscosity of 750 mPa·s to 4,000 mPa·s, as measured with a Brookfield spindle viscometer (model LVT) at 25° C. and a rotary speed of 30 rpm with spindles of size No. 2 or No. 3 using a 2% aqueous solution, and a high viscosity CMC having a viscosity of 4,000 mPa·s to 25,000 mPa·s, as measured with a Brookfield spindle viscometer (model LVT) at 25° C. and a rotary speed of 30 rpm with spindles of size No. 3 or 4 using a 1% aqueous solution.

The CMC used herein may have any degree of substitution such as 0.20 to 1.50. Preferably, the degree of substitution is from 0.40 to 1.10, more preferably from 0.60 to 0.95, and most preferably from 0.70 to 0.90. As used herein, the "degree of substitution" (degree of etherification) is defined as follows: $[C_6H_7O_2(OH)_x(OCH_2COO_m)_y]_n$, where n is the degree of polymerization (e.g., 450 to 4.000) and x+y=3, wherein y is the degree of substitution. The degree of substitution can be determined as known in the art (e.g., according to the method described in the International Oenological Codex COEI-1-CMC:2009).

Within the context of the present invention, the dermal filler composition may further comprise a local anesthetic agent to mitigate pain upon injection. Suitable local anesthetic agents for use herein include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof, and combinations thereof. Preferably, the anesthetic agent is lidocaine, such as in the form of lidocaine HCl. The lidocaine, e.g. lidocaine HCl, may be present in the dermal filler composition in a concentration of from 0.01 wt. % to 5 wt. %, preferably from 0.1 wt. % to 1.0 wt. %, and particularly preferred at a concentration of 0.3 wt. % (c)/0 w/w).

In addition, the dermal filler composition of the present invention may further comprise one or more compounds selected from the group consisting of polyols, vitamins, amino acids, antioxidants, and mineral salts.

Suitable polyols include, but are not limited to, glycerin, mannitol, sorbitol, propylene glycol, erythritol, xylitol, maltitol, and lactitol. Particularly suitable for use herein is glycerin, optionally in combination with one or more of the aforementioned polyol compounds. Another particularly suitable polyol is mannitol, either alone or in combination with another polyol, especially glycerin. The polyol(s) may, for example, be included in the dermal filler composition at a concentration of 0.1% to 20% (w/w), 1% to 15% (w/w) or 2% to 10% (w/w), in particular at a concentration of 5% to 8% (w/w).

Suitable vitamins that may be used within the present invention include vitamin C, vitamin E and vitamins of the B group, i.e. one or more of $B_1$, $B_2$, $B_3$, $B_5$, $B_6$, $B_7$, $B_9$ and $B_{12}$ vitamins. The vitamins may be present to stimulate and maintain cellular metabolism and, thus, to promote collagen production. Particularly preferred for use herein is vitamin C, vitamin E and vitamin $B_6$.

Suitable antioxidants that may be used herein include, for example, ascorbic acid and derivatives thereof. Mineral salts that can be used in the context of the present invention include, for example, transition metal salts, alkali metal salts and alkaline earth metal salts. A preferred mineral salt for use herein is a zinc salt.

Preferably, the dermal filler composition comprises (i) at least one polyol, in particular glycerin, (ii) at least one local anesthetic agent, in particular lidocaine, (iii) at least one polyol, in particular glycerin, and at least one local anesthetic agent, in particular lidocaine, (iv) no lidocaine, or (v) at least one polyol, in particular glycerin, and no local anesthetic agent, in particular no lidocaine, wherein said at least one polyol (in particular glycerin) and said at least one local anesthetic agent are included in the dermal filler composition in the concentrations mentioned herein above, e.g., 2 wt. % to 10 wt. % and 0.1 wt. % to 1.0 wt. %, respectively. In accordance with the present invention, a preferred composition, including compositions (i) to (v), may further contain an antioxidant.

It is further contemplated herein that the injectable dermal filler composition may include non-crosslinked polymers other than CMC. For example, the injectable dermal filler composition may further comprise 0.001% to 15% (v/v), in particular 1% to 10% (v/v) non-crosslinked HA. The average molecular weight of the non-crosslinked HA may range from $1.0 \times 10^6$ Da to $4.0 \times 10^6$ Da. The non-crosslinked hyaluronic acid functions as a lubricant to facilitate extrusion of the dermal filler composition from a syringe. Preferably, the dermal filler composition of the present invention does not contain any other crosslinked polymer than crosslinked hyaluronic acid and/or does not contain any non-crosslinked polymer other than CMC and the optionally present non-crosslinked HA.

The dermal filler composition of the present invention is generally sterilized. The method of choice for sterilization is sterilization by moist heat (e.g., autoclaving). For example, the dermal filler composition described herein may be filled into syringes and then sterilized by moist heat (e.g., autoclaving at 121° C.) as known in the art.

Moreover, in accordance with the present invention, the dermal filler composition, particularly the sterile filler composition, e.g. the dermal filler composition after sterilization by moist heat such as autoclaving, may have one, two or all three of the following properties:
(i) an elastic modulus G' at a frequency (f) of 0.4 Hz and 25° C. of from 10 Pa to 600 Pa, preferably from 20 Pa to 400 Pa or from 30 Pa to 200 Pa, more preferably from 40 Pa to 150 Pa or from 50 Pa to 100 Pa;
(ii) a viscosity at a frequency of 0.4 Hz and 25° C. of from 5 Pa·s to 300 Pa·s, preferably from 10 Pa·s to 200 Pa·s or from 15 Pa·s to 100 Pa·s, more preferably from 20 Pa·s to 75 Pa·s or from 25 Pa·s to 50 Pa·s; and
(iii) a tan delta (G"/G') at a frequency of 0.4 Hz and 25° C. of from 0.20 to 0.80, preferably from 0.30 to 0.70 or from 0.35 to 0.60, more preferably from 0.40 to 0.55 or from 0.45 to 0.50.

In addition, the extrusion force for the dermal filler composition according to the present invention does typically not exceed 15 N and, preferably, does not exceed 10 N, and may be in the range of from 2 N to 15 N, preferably from 3 N to 10 N, more preferably from 4 N to 9 N, as measured through a (e.g., Terumo K pack II) 27 G TW ¾ needle at an extrusion rate of about 12.7 mm/min (0.5 inch/min) using a standard 1.5 ml syringe (e.g., a 1.5 ml glass or plastic syringe).

In a second aspect, the present invention relates to a process for preparing a dermal filler composition of the present invention as described herein, the process comprising:
(a) preparing a crosslinked hyaluronic acid gel using 1,4-butanediol dig ycidyl ether as crosslinking agent,
(b) mixing the crosslinked hyaluronic add gel prepared in step (a) with carboxymethyl cellulose and calcium phosphate material particles of which at least 90% (w/w) have a particle size of less than 60 μm.

This process may further comprise the step of sterilization the dermal filler composition by moist heat, preferably by autoclaving. The dermal filler composition is usually filled into syringe before sterilization and then sterilized by moist heat to provide sterile, ready-to-use prefilled syringes. Autoclaving may be carried out, for example, at a temperature of 121° C. for 0.5 min to 2 min.

The crosslinked hyaluronic acid gel prepared in step (a) and/or the carboxymethyl cellulose, for example provided in the form of a gel, of step (b) may comprises one or more of the polyols mentioned above, in particular glycerin. Additionally, or alternatively, one or more of the polyols mentioned above, in particular glycerin, may also be added after step (b). Likewise, the crosslinked hyaluronic acid gel prepared in step (a) and/or the carboxymethyl cellulose, for example provided in the form of a gel, of step (b) may comprises one or more local anesthetic agents mentioned above, in particular lidocaine. Additionally, or alternatively, one or more of the anesthetic agents mentioned above, in particular lidocaine, may also be added after step (b).

Furthermore, within the present invention, the calcium phosphate material particles may be suspended in the carboxymethyl cellulose gel or, alternatively, the calcium phosphate material particles may be mixed together with the crosslinked hyaluronic acid gel and the carboxymethyl cellulose in step (c). The calcium phosphate material particles may also be added to the mixture obtained in step (c), or may be present during the crosslinking of HA to give a calcium phosphate material particles containing, crosslinked HA.

In a preferred embodiment of the present invention, step (b) comprises mixing the crosslinked hyaluronic acid gel prepared in step (a) with carboxymethyl cellulose, calcium phosphate material particles of which at least 90% (w/w) have a particle size of less than 60 μm, at least one polyol (preferably glycerin, in particular in an amount so as to result in a concentration in the final dermal filler composition of 2-10% (w/w)), and at least one local anesthetic agent (preferably lidocaine (e.g., lidocaine-HCl), in particular in an amount so as to result in a concentration in the final dermal filler composition of 0.1-1.0% (w/w)).

In a third aspect, the present invention relates to a prefilled syringe, or a part thereof, filled with the dermal filler composition of the present invention. The prefilled syringe may by a ready-to-use syringe with a tip cap or a pre-mounted needle. A prefilled syringe part may be, for example, a syringe barrel provided at the distal end thereof with a tip being closed by a closing member and having a closed proximal end, said barrel being prefilled with the dermal filler composition of the present invention.

In a fourth aspect, the present invention relates to a kit comprising the prefilled syringe, or part thereof, according to the present invention, and optionally instructions for use.

In a fifth aspect, the present invention relates to the use of a dermal filler composition of the present invention for cosmetic treatments. Preferably, the dermal filler composition of the present invention is used for improvement of skin quality of, e.g., the décolleté, neck and face (mid to lower face). Other potential treatment sites include, e.g., hands, thighs, arms, abdomen and buttocks.

In particular, the dermal filler composition of the present invention may be used for reduction of skin laxity (i.e. skin tightening), increasing skin elasticity, improvement of evenness of skin tone, enhancement of skin hydration, restoration of hydrobalance, retaining skin moisture, enhancing skin radiance, revitalization of the skin, and achieving a natural glowing look.

Furthermore, the dermal filler composition of the present invention may be used as tissue augmenting or filling material, in particular for the cosmetic treatment of wrinkles and lines of the skin (e.g., facial lines and facial wrinkles), more particular for the reduction of fine lines (e.g. in the face or other body parts).

In a sixth and last aspect, the present invention relates to a method for replacing or filling of a biological tissue or increasing the volume of the biological tissue, comprising administering to a subject in need thereof an effective amount of the dermal filler composition of the present invention.

The injectable dermal filler composition is generally administered by injection such as by subcutaneous or intradermal injection. The term "effective amount" refers to the amount of the injectable dermal filler composition sufficient to effect beneficial or desired cosmetic (aesthetic) results. A "subject" in the sense of the present invention is any individual or patient in need of the cosmetic treatment.

The dermal filler composition is administered for cosmetic purposes, in particular for improvement of skin quality and treatment of wrinkles and lines of the skin, as explained above. With respect to the composition of the dermal filler composition, its manufacturing method and uses, and definitions of technical terms, it is referred to the above that equally applies here.

The present invention will now be further illustrated by the following, non-limiting examples.

EXAMPLES

The examples provided below demonstrate that crosslinked hyaluronic acid (HA) in combination with carboxymethyl cellulose (CMC) is capable of keeping calcium phosphate material particles in stable suspension while providing the unique "liquid like" properties of diluted Radiesse.

The abbreviations used in the sections that follow are as follows:
CaHA: calcium hydroxyapatite
(Na)HA: (sodium) hyaluronic acid
(Na)CMC: (sodium) carboxymethyl cellulose
cHA: crosslinked hyaluronic acid
G': storage modulus (elastic modulus) [Pa]
G'': loss modulus (viscous modulus) [Pa]
Tanδ: Tan Delta (loss tangent;=G''/G')
absolute complex viscosity [Pa·s]

Rheological measurements. The rheological measurements of G' and Tanδ were performed using an Anton Paar MCR 302 rheometer equipped with a plate-plate system with a diameter of 20 mm and the following settings: T=30° C., gap size=1.0 mm, plate size=PP35, tau (stress)=5 Pa, frequency range: 0.1-10 Hz, frequency/decade: 6.

Suspension stability. The suspension stability of the formulations was determined by a decantation assay. The steam sterilized syringes prefilled with the gel samples were stored at 25° C./60% room humidity and at 40° C./75% room humidity for a maximum period of three months in upright position with the syringe tip pointing downwards. From time to time, the syringes were visually inspected as to whether gravity-driven phase separation occurred, generally indicated by the upper phase being clarified compared to the lower phase. This is referred to "decantation" herein, and is not meant to indicate or require complete settling of the CaHA particles.

Organoleptic assessment. The organoleptic (sensory) assessment of the dermal filler compositions was carried out using a trained testing panel of 4 persons. The test is described in Garg et al., "Spreading of semisolid formulations: An update", Pharmaceutical Technology, September 2002, pp. 82-105. In brief, the test persons assessed the properties of the sample by applying a small portion of the product between the thumb and trigger finger. The sample was then squeezed and stretched between the two fingers and rated as follows: (1) too strong and/or too cohesive, (2): slightly too strong and/or slightly too cohesive, (3): ok (i.e. comparable to Radiesse 1:1 diluted in water for injection (WFI)). If all four panelists assigned scoring rate (3), the overall sensory quality was rated "+" (good). If only two or three panelists assigned scoring rate (3), the overall sensory quality was rated "o" (mediocre). If only one or none of the panelists assigned scoring rate (3), the overall sensory quality was rated "−" (poor).

Spreadability. The spreadability (i.e. the ease of which a product can be spread) was assessed using the Two Plate Test. This test is described in Garg et al., "Spreading of semisolid formulations: An update", Pharmaceutical Technology, September 2002, pp. 82-105, and is commonly used for determining and quantifying the spreadability of semisolid preparations. To measure the surface area of the sample in cm², a millimeter scale paper was placed below a glass ground plate. Then, 330±10 mg of sample were placed on the ground plate (VWR no. HECH41042030; Petri dish, ø=120 mm) and covered by a top glass plate (ThermoScientific no. 630-2128; ø=50 mm; thickness #0). A certified (VWR no. 611-8373) 10 g standard weight was put on the top plate. After one minute a picture of the sample was taken from the top and the surface area was analyzed with Adobe Acrobat. The area was manually integrated by using the Adobe measurement tool. A distance of 10 mm on the picture was used for calibration.

Firmness and work of shear. The firmness and work of shear were determined using the TA-RIG test. The TA-RIG test is one of the default methods provided by the texture analyzer TA.XTPlus (Texture Technologies Corp.) and is commonly used for measuring physical characteristics of all type of products, including pharmaceutical and food products. For this test a specific measuring rig of precisely matched test container and a perspex cone were used. The sample was filled into the test container and the cone penetrated the test container filled with product. The force increases up to the point of the maximum penetration depth of the cone probe. This peak force value (maximum force to shear) was taken as the "firmness" at the specified depth, and characterizes the degree of softness of the sample. Moreover, a firmer sample also shows a correspondingly larger area, which represents the total amount of force required to perform the shearing process. This is referred to as "work of shear" and was also determined. The work of shear corresponds to a one-newton force applied for one second.

Extrusion force. The extrusion force was determined through a 27G ¾" needle (Terumo K pack II) at an extrusion rate of 12.7 mm/min using a standard 1.5 ml syringe (1.5 ml plastic syringe) by means of a Texture analyzer TA.XTPlus (Texture Technologies Corp.).

Example 1

Preparation of Dermal Fillers Based on cHA, CMC and CaHA (Samples S1 to S12

Samples S1 to S12 (see TABLE 1) were prepared in that CaHA particles having a particle size of 25 µm to 45 µm were mixed with a phosphate buffer solution of NaCMC by shaking 2 h at 98 rpm, and leaving the mixture overnight at 5° C. The used phosphate buffer solution of NaCMC also contained a respective amount of lidocaine (lidocaine-HCl) and glycerol to obtain 0.3% (w/v) of lidocaine and 8.52% (w/w) of glycerol in the final dermal filler samples. Next, the obtained mixture was mixed with a phosphate buffer solution of NaCMC and cHA (cHA corresponding to the "MHA gel" described herein) in two 60 ml cartridges connected with a 314SS female/female Luer connector. The gel was mixed using a 4 bar air pressure controller with two NORDSON pressure Ultimus 1. For all samples 10 cycles were performed to ensure complete mixing. After mixing, the samples were filled into 1 ml syringes and steam sterilized.

Example 2

Preparation of Radiesse 1:1 (Comparative Sample C1

For comparison purposes, about 1.5 ml of the commercial sterile filler product Radiesse were transferred into a 5 ml plastic syringe using a female-to-female connector. A second 5 ml plastic syringe was filled with 1.5 ml water for injection (WFI). The syringes were connected and the Radiesse was mixed with the WFI by alternately depressing the plunger until the product was mixed homogenously (at least 10 mixing strokes).

Example 3

Preparation of Radiesse-HA (Comparative Sample C2

As another comparison, a cHA/CaHA gel with 15% (v/v) CMC as lubrication phase was prepared as described in Example 6 of WO 2016/074794 A1 (hereinafter referred to as "Radiesse-HA"). More specifically, in a first step, a HA "cake" was prepared by dissolving 43 g NaHA (mean molecular weight of about 2.8 MDa) in 270.35 g of phosphate buffer.

In separate steps, an alkaline solution was made by dissolving 3.31 g of solid sodium hydroxide in 10 ml of phosphate buffer. Moreover, a BDDE solution was prepared by mixing 12.5 g of 2M NaOH solution with 88.5 g of phosphate buffer, and mixing 8.21 ml of the obtained solution with 3.395 ml of BDDE.

The HA cake was manually broken into small pieces in a mixing bowl, the whole alkaline solution was added to the bowl, followed by mixing for 30 to 40 minutes at 12 rpm. Then, the BDDE solution was added to the bowl and the mixing was continued for 10 to 15 minutes at 25 rpm. The temperature set point was changed to 33.33° C. and the mixture was left for 4 hours at this temperature.

A neutralization solution was prepared by adding 920.99 g of buffer to 84.62 g of 1 M HCl. The whole neutralization solution was then added into the bowl and stirred for 2 hours at 5° C. Afterwards, the gel was purified according to methods known to those skilled in the art (e.g., dialysis) to obtain a crosslinked HA gel ("MHA gel").

In a next step, the obtained MHA gel was used to prepare a gel formulation that further comprises lidocaine and glycerol ("MHAG gel"). First, a concentrated lidocaine solution "LS1" was prepared by adding 2 g of lidocaine to 2 g of phosphate buffer, followed by gentle stirring using a magnetic stirrer until complete dissolution. Then, 467 g of the MHA gel was mixed with 2116 µl of the LS1 solution for 15 minutes using a mixer. 33 g of glycerin were added and mixed moderately for 1.5 hours to obtain a gel formulation referred to as the "MHAG gel".

Afterwards, 168.266 g of glycerin were added to 223.29 g of phosphate buffer under stirring using a magnetic stirrer until complete dissolution. 8.529 g of NaCMC were added and strongly mixed for 1 hour to obtain solution "LB5".

To prepare a cHA/CaHA gel with 15% (v/v) CMC lubricant, 280.02 g of CaHA (25 µm to 45 µm), 78.46 g of LB5 and 141.562 g of the MHAG gel were placed in a mixing bowl. Then, 2.120 ml of a lidocaine solution (2 g of lidocaine in 2 g of phosphate buffer) were added. The mixture was stirred at moderate speed for 1.5 hours. After degasing under vacuum, 1 ml syringes were filled and sterilized at 121° C. for 20 minutes.

Example 4

Effects of Adding cHA to CaHA/CMC Dermal Filler Compositions in Terms of Stability, Rheological Properties and Sensory Characteristics The suspension stability, rheological properties and sensory characteristics of Samples S1-S12 as prepared in Example 1 were assessed using the methods described hereinabove. The results are shown in TABLE 1.

TABLE 1

Stability, rheological and sensory properties of sterile dermal filler compositions with varying amounts of CaHA particles, CMC and cHA

| No. | CaHA [% w/w] | NaCMC [mg/g gel]* | cHA [mg/g gel] | Decantation (dc)** | $G'_{[0.4Hz]}$ [Pa] | $Tan\delta_{[0.4Hz]}$ | $\|\eta^*\|_{[0.4Hz]}$ [Pa·s] | Sensory Test |
|---|---|---|---|---|---|---|---|---|
| S1 | 12.29 | 1.39 | 14.02 | no | 144 | 0.288 | 60 | − |
| S2 | 12.29 | 2.33 | 9.98 | no | 87 | 0.332 | 36 | ○ |
| S3 | 12.29 | 3.27 | 5.94 | dc (d = 10) | 24 | 0.827 | 12 | + |
| S4 | 12.29 | 2.10 | 14.02 | no | 146 | 0.310 | 61 | − |
| S5 | 12.29 | 3.47 | 9.98 | no | 92 | 0.357 | 39 | ○ |
| S6 | 12.29 | 4.87 | 5.94 | dc (d = 10) | 27 | 0.791 | 13 | + |
| S7 | 12.29 | 2.78 | 14.02 | no | 152 | 0.322 | 64 | − |
| S8 | 12.29 | 4.66 | 9.98 | no | 103 | 0.368 | 44 | ○ |
| S9 | 12.29 | 6.47 | 5.94 | yes | 37 | 0.683 | 18 | ○ |
| S10 | 20.02 | 2.60 | 7.00 | no | 52 | 0.492 | 23 | + |
| S11 | 20.02 | 3.90 | 7.00 | no | 59 | 0.495 | 26 | + |
| S12 | 20.02 | 5.19 | 7.00 | no | 66 | 0.508 | 29 | ○ |

*mg NaCMC based on 1 g of entire gel phase (the sample formulation without CaHA particles)
**Decantation after three months, if not otherwise stated (d-day)

As can be seen from TABLE 1, the suspension stability is reduced for samples having a cHA concentration of below 6 mg/g (cf. samples S3, S6 and S9), as indicated by phase separation due to settling. In addition, at cHA concentrations of below 6 mg/g, the G' values are significantly decreased while the Tanδ values are significantly increased. If, however, the cHA concentration exceeds 10 mg/g (see samples S1, S4 and S7), the sensory properties tend to be deteriorated as indicated by the negative sensory test results. Thus, a concentration of cHA of about 6 mg/g to about 10 mg/g was found to be suitable for effectively keeping the CaHA particles in suspension while allowing the dermal filler to exhibit favorable rheological and sensory properties.

Example 5

Comparison of an Inventive Dermal Filler with 1:1 Diluted Radiesse, Radiesse-HA and Radiesse The rheological and sensory properties of sample S11 of the present invention (Inventive Sample) were compared with those of 1:1 (WFI) diluted Radiesse prepared according to Example 2 (Comparative Sample C1) and those of Radiesse-HA prepared according to Example 6 of WO 2016/074794 A1 (Comparative Sample C2). In addition, Radiesse was used as Comparative Sample C3. The results are shown in TABLE 2 (the sensory test results are shown relative to Comparative Sample C1).

TABLE 2

Comparison of inventive dermal filler S11 with Radiesse (1:1 dilution), Radiesse-HA and Radiesse in terms of their rheological and sensory properties (EF = extrusion force; ST = sensory test)

| Sample | Product | CaHA [% w/w] | NaCMC [mg/g gel] | HA [mg/g gel] | Decantation (dc)** | $G'_{[0.4Hz]}$ [Pa] | $Tan\delta_{[0.4Hz]}$ | $\|\eta^*\|_{[0.4Hz]}$ [Pa·s] | EF [N] | ST |
|---|---|---|---|---|---|---|---|---|---|---|
| S11 | Dermal filler of invention | 20 | 3.90 | 7.00 | no dc | 59 | 0.495 | 26 | 7.25 | + |
| C1 | Radiesse (1:1 dilution) | 28 | 1.58 | — | dc at 0.5 days | 23 | 1.192 | 14 | 8.45 | n.a. (ref.) |
| C2 | Radiesse-HA (Ex. 6 WO'794) | 28 | 7.60 | 14.01 | no dc | 1036 | 0.375 | 440 | 23.01 | − |
| C3 | Radiesse | 56 | 3.2 | — | na | 1061 | 0.580 | 488 | 17.13 | − |

*mg NaCMC based on 1 g of entire gel phase (the sample formulation without CaHA particles)
**Decantation after three months, if not otherwise stated (d = day)

In addition to the parameters shown in TABLE 2, the surface area (a measure of spreadability) was measured using the Two Plate Test and the firmness and shear characteristics were determined using the TA-RIG test. Sample S11 of the present invention (Inventive Sample) was compared with Comparative Samples C1, C2 and C3. The results are shown in TABLE 3.

TABLE 3

Comparison of inventive dermal filler S11 with Radiesse (1:1 dilution), Radiesse-HA and Radiesse in terms of their surface area, firmness and shear characteristics.

| Sample | Product | Two Plate Test Surface area [cm²/g] | TA-RIG Firmness [N] | TA-RIG Shear [N · s] |
|---|---|---|---|---|
| S11 | Dermal filler of invention | 17.1 | 2.7 | 2.2 |
| C1 | Radiesse (1:1 dilution) | 18.6 | 1.9 | 1.5 |
| C2 | Radiesse-HA (Ex. 6 of WO'794) | 4.9 | 20.9 | 17.8 |
| C3 | Radiesse | 4.8 | 20.8 | 19.5 |

As is evident from TABLE 3, the surface area measured for the S11 dermal filler of the present invention is very similar to the surface area measured for 1:1 diluted Radiesse. In contrast, the surface area of Comparative Sample C2 (Radiesse-HA) and of Comparative Sample C3 (Radiesse) is markedly lower indicating that the product spreads less under the skin and is therefore not suitable for the treatment of large skin areas. Similarly, the firmness and shear values measured for the S11 dermal filler of the present invention and 1:1 diluted Radiesse are in a comparable range and relatively low, whereas the corresponding firmness and shear values measured for Comparative Sample C2 (Radiesse-HA) and Comparative Sample C3 (Radiesse) are significantly higher. Thus, the S11 formulation of the present invention is highly similar to 1:1 diluted Radiesse.

Overall, the results demonstrate that the dermal filler of the present invention is stable in respect to separation of CaHA particles and at the same time exhibits the unique "liquid like" sensory, rheological and mechanical properties of diluted Radiesse.

The invention claimed is:

1. A dermal filler composition comprising:
a gel phase comprising:
from 6 mg/g to 10 mg/g crosslinked hyaluronic acid crosslinked with 1,4-butanediol diglycidyl ether based on the total weight of the gel phase, and
from 2 mg/g to 5 mg/g carboxymethyl cellulose based on the total weight of the gel phase; and
a solid phase comprising from 12% (w/w) to 20% (w/w) calcium phosphate material particles based on the total weight of the dermal filler composition,
wherein at least 90% (w/w) of the calcium phosphate material particles have a particle size of less than 60 μm, and
wherein the solid phase is suspended in the gel phase.

2. The dermal filler composition of claim 1, wherein the hyaluronic acid used for preparation of the crosslinked HA has an average molecular weight of $0.5 \times 10^6$ Da to $4.5 \times 10^6$ Da.

3. The dermal filler composition of claim 1, wherein at least 90% (w/w) of the calcium phosphate material particles have a particle size of from 10 μm to less than 60 μm or from 25 μm to 45 μm, or less than 25 μm.

4. The dermal filler composition of claim 1, wherein the calcium phosphate material particles are selected from calcium hydroxyapatite, calcium fluoroapatite, calcium chloroapatite, calcium carbonate apatite, tetracalcium phosphate, calcium pyrophosphate, tricalcium phosphate, octacalcium phosphate particles, and mixtures thereof.

5. The dermal filler composition of claim 1, wherein the carboxymethyl cellulose has an average molecular weight of $5.0 \times 10^4$ Da to $1.5 \times 10^6$ Da, or a degree of substitution of 0.20 to 1.50, or both.

6. The dermal filler composition of claim 1, further comprising lidocaine, or one or more local anesthetic agents other than lidocaine, or both.

7. The dermal filler composition of claim 1, further comprising one or more compounds selected from the group consisting of polyols, vitamins, amino adds, metals, antioxidants, and mineral salts.

8. A process for preparing a dermal filler composition according to claim 1, the process comprising:
(a) preparing a crosslinked hyaluronic acid gel using 1,4-butanediol diglycidyl ether as crosslinking agent,
(b) mixing the crosslinked hyaluronic acid gel prepared in step (a) with carboxymethyl cellulose, or a salt thereof, and calcium phosphate material particles of which at least 90% (w/w) have a particle size of less than 60 μm.

9. The process of claim 8, further comprising sterilizing the mixture of (b) by moist heat.

10. A prefilled syringe, or a part thereof, filled with a dermal filler composition according claim 1.

11. A kit comprising the prefilled syringe, or a part thereof, according to claim 10, and optionally instructions for use.

12. A product comprising a dermal filler composition according to claim 1 for cosmetic treatments.

13. A method of improving skin quality or reducing wrinkles or lines of the skin comprising administering to a subject in need thereof an effective amount of the dermal filler composition of claim 1.

14. The dermal filler composition of claim 1, wherein the calcium phosphate material particles comprise calcium hydroxyapatite.

15. The dermal filler composition of claim 1, wherein the calcium phosphate material particles are calcium hydroxyapatite particles.

* * * * *